United States Patent
Lim et al.

(10) Patent No.: US 11,590,331 B2
(45) Date of Patent: Feb. 28, 2023

(54) DISSOLVING MICRONEEDLE PATCHES COMPRISING CORTICOSTEROID

(71) Applicants: MICROPOINT TECHNOLOGIES PTE LTD, Singapore (SG); NATIONAL SKIN CENTRE (S) PTE LTD, Singapore (SG)

(72) Inventors: Chee Yen Lim, Singapore (SG); Hong Liang Tey, Singapore (SG)

(*) Notice: Subject to any disclaimer, the term of this patent is extended or adjusted under 35 U.S.C. 154(b) by 627 days.

(21) Appl. No.: 16/500,203

(22) PCT Filed: Jan. 10, 2019

(86) PCT No.: PCT/SG2019/050014
§ 371 (c)(1),
(2) Date: Oct. 2, 2019

(87) PCT Pub. No.: WO2019/135717
PCT Pub. Date: Jul. 11, 2019

(65) Prior Publication Data
US 2020/0206488 A1    Jul. 2, 2020

(30) Foreign Application Priority Data
Jan. 3, 2018 (SG) .......................... 10201800072Y (51) Int. Cl.
*A61M 37/00* (2006.01)
*A61K 9/00* (2006.01)
*A61K 31/57* (2006.01)

(52) U.S. Cl.
CPC ....... *A61M 37/0015* (2013.01); *A61K 9/0021* (2013.01); *A61K 31/57* (2013.01);
(Continued)

(58) Field of Classification Search
CPC ...... A61M 37/0015; A61M 2037/0023; A61M 2037/0046; A61M 2037/0053; A61M 2207/10; A61K 9/0021
See application file for complete search history.

(56) References Cited

U.S. PATENT DOCUMENTS 9,539,418 B2    1/2017  Quan et al.
2003/0135161 A1* 7/2003  Fleming ............. A61B 5/14514
                                                           606/186
(Continued)

FOREIGN PATENT DOCUMENTS

JP    2007-001938 A    1/2007
JP    2010-082401 A    4/2010
(Continued)

OTHER PUBLICATIONS

International Search Report of PCT/SG2019/050014 dated Apr. 23, 2019.

*Primary Examiner* — Amber R Stiles
(74) *Attorney, Agent, or Firm* — Patshegen IP; Moshe Pinchas (57) ABSTRACT

In the preferred embodiment of the present invention, a patch of dissolving microneedles loaded with active ingredients to be applied to skin for treating skin conditions is provided. As seen in FIG. 1, the dissolving microneedle patch (10) comprises a substrate (12) and a plurality of microneedles (14) which extends from the substrate. The dissolving microneedle patch (10) is made of a matrix material and at least one active ingredient such as a corticosteroid, namely triamcinolone (TAC). The matrix material is made of bio-compatible materials such as hyaluronic acid (HA), polyvinylpyrrolidone (PVP), or mixture of them, which dissolve rapidly when they are in contact with the inner skin. The active ingredient is loaded onto individual (Continued)

patches with the desirable dosage ranging from 0.01 mg-1.0 mg.

7 Claims, 6 Drawing Sheets

(52) U.S. Cl.
CPC ............... *A61M 2037/0023* (2013.01); *A61M 2037/0046* (2013.01); *A61M 2037/0053* (2013.01); *A61M 2207/10* (2013.01)

(56) References Cited

U.S. PATENT DOCUMENTS

| | | | | |
|---|---|---|---|---|
| 2004/0265354 A1* | 12/2004 | Ameri | ..................... | A61P 35/00 |
| | | | | 514/10.8 |
| 2008/0269685 A1* | 10/2008 | Singh | ................... | A61K 9/0021 |
| | | | | 604/173 |
| 2011/0028905 A1* | 2/2011 | Takada | ............... | A61K 31/7048 |
| | | | | 604/180 |
| 2013/0012882 A1 | 1/2013 | Quan et al. | | |

FOREIGN PATENT DOCUMENTS

| | | |
|---|---|---|
| JP | 2013-032324 A | 2/2013 |
| JP | 2014-023697 A | 2/2014 |
| JP | 2015-016362 A | 1/2015 |
| JP | 2015-151380 A | 8/2015 |
| JP | 2017-051354 A | 3/2017 |
| JP | 2010-233674 A | 10/2019 |
| WO | 2011/115272 A1 | 9/2011 |

* cited by examiner

DISSOLVING MICRONEEDLE PATCHES COMPRISING CORTICOSTEROID

CROSS-REFERENCE TO RELATED APPLICATIONS

This application is a § 371 national phase application of PCT/SG2019/050014 filed Jan. 10, 2019 entitled "DISSOLVING MICRONEEDLE PATCHES COMPRISING CORTICOSTEROID," which claims the benefit of and priority to Singapore Patent Application No. 10201800072Y filed Jan. 3, 2018, the contents of which being incorporated by reference in their entireties herein.

FIELD OF THE INVENTION

The present invention generally relates to home-based treatments for skin conditions. More particularly, the present invention pertains to drug-laden microneedle patches having tailored shapes for treating chronic skin conditions such as keloids, etc.

BACKGROUND OF THE INVENTION

Keloid scars are a common skin disorder with significant morbidity. Prominent symptoms include pain and itch which can significantly impact the quality of life. The undesirable, disfiguring appearance can also lead to emotional distress and psychosocial burden. Current therapeutic options are limited. The first-line option is intra-lesional corticosteroid injections which, due to the sensitivity of keloids, is painful and precludes treatment in many patients. Moreover, there is a high recurrence rate of near 50% Other commonly employed therapies include cryotherapy, radiotherapy and occlusive dressings which have poor efficacy rates, low patient adherence and a high rate of recurrence.

At the National Skin Centre (NSC) in Singapore, in 2012, there were 675 new cases of keloids seen. Statistics show that keloids account for 11.5-34.5 million surgical procedures globally and represent a SGD $7 billion market size. Given the incidence of keloids both locally and worldwide and the limitations with current treatment, there is clearly an unmet need for more effective, tolerable, and reliable therapy.

The current treatment is direct injection of corticosteroid into the keloids using syringes, which is painful. If the keloids cover a large area on the skin, multiple injections are performed to spread the corticosteroid over the entire keloids as uniform as possible. This requires great dexterity and dermatological experience and is normally carried out by a specialist or medical personnel. The shortcomings of the present practice are that the parenteral injection is painful and it is almost impossible to spread the drug evenly across the keloid, even with experienced medical personnel.

Over the past decade, microneedle technology has been increasingly tried for the treatment of skin conditions. The decreased likelihood of causing pain, infection, and injury makes microneedles a great platform for self-administration of drugs. In recent years, drug-loaded dissolving hyaluronic acid microneedles have received extensive attention in transdermal drug delivery. In contrast to drug-coated microneedles, they do not have the risk of leaving foreign material in the skin if broken, can encapsulate sensitive biomolecules within the needle shafts to deliver a specific dosage of drugs, and may have a higher drug-loading capacity.

In particular, microneedle patches are advantageous in treating keloids because the microneedles can deliver the corticosteroid into the keloids painlessly and easily without needing the help of trained medical personnel. Moreover, the microneedle patches can be custom-made into individual keloids' shapes so that the corticosteroid is delivered to and spread evenly over the keloids' site, without spilling over to the normal skin, as corticosteroid is harmful to normal skin.

U.S. Pat. No. 9,539,418 B2 awarded to Cosmed Pharmaceutical reported a microneedle patch made of proteoglycan and U.S. Pat. No. 8,167,152 B2 awarded to Cosmed Pharmaceutical reported a microneedle patch made of hyaluronic acid and collagen. Both patents report dissolving microneedles but they do not contain drug for treating skin conditions such as keloids.

PCT Patent Publication No. WO 2015/122838A1 assigned to Lim et. al. reported a rapidly dissolvable microneedle and the fabrication method thereof, which is reference in its entirety in this present invention.

To our knowledge, there is no published data on the use of drug-embedded dissolving microneedles in the treatment of keloids. As such, the motivation of the present invention is to provide a home-based solution where a custom-shaped microneedle patch loaded with corticosteroid can be applied by a patient at home on daily or weekly basis. The present invention bring forth a is translates to less pain, improved efficacy, feasibility for self-administration, better patient adherence and a lower risk of systemic absorption and local side effects of steroid therapy.

BRIEF SUMMARY OF THE INVENTION

The current practice in treating chronic skin conditions which require constant injection of drugs on the affected skin sites, poses several problems as follows:
 (a) the trauma they experience during the intradermal injections,
 (b) the inconvenience they endure for every visit to the hospital for such injections,
 (c) the uneven delivery of drug across the skin sites (e.g. keloids) by hands, Considering these problems, there is a long-felt need for a drug delivery system to provide certain desirable features such as:
 (a) painlessness,
 (b) self-administration, and
 (c) precision in drug delivery in terms of depth and affected area.

Now embodiments of the present invention will be provided to solve the current problems of chronic skin conditions by providing the desirable solutions mentioned above.

Figure 1:
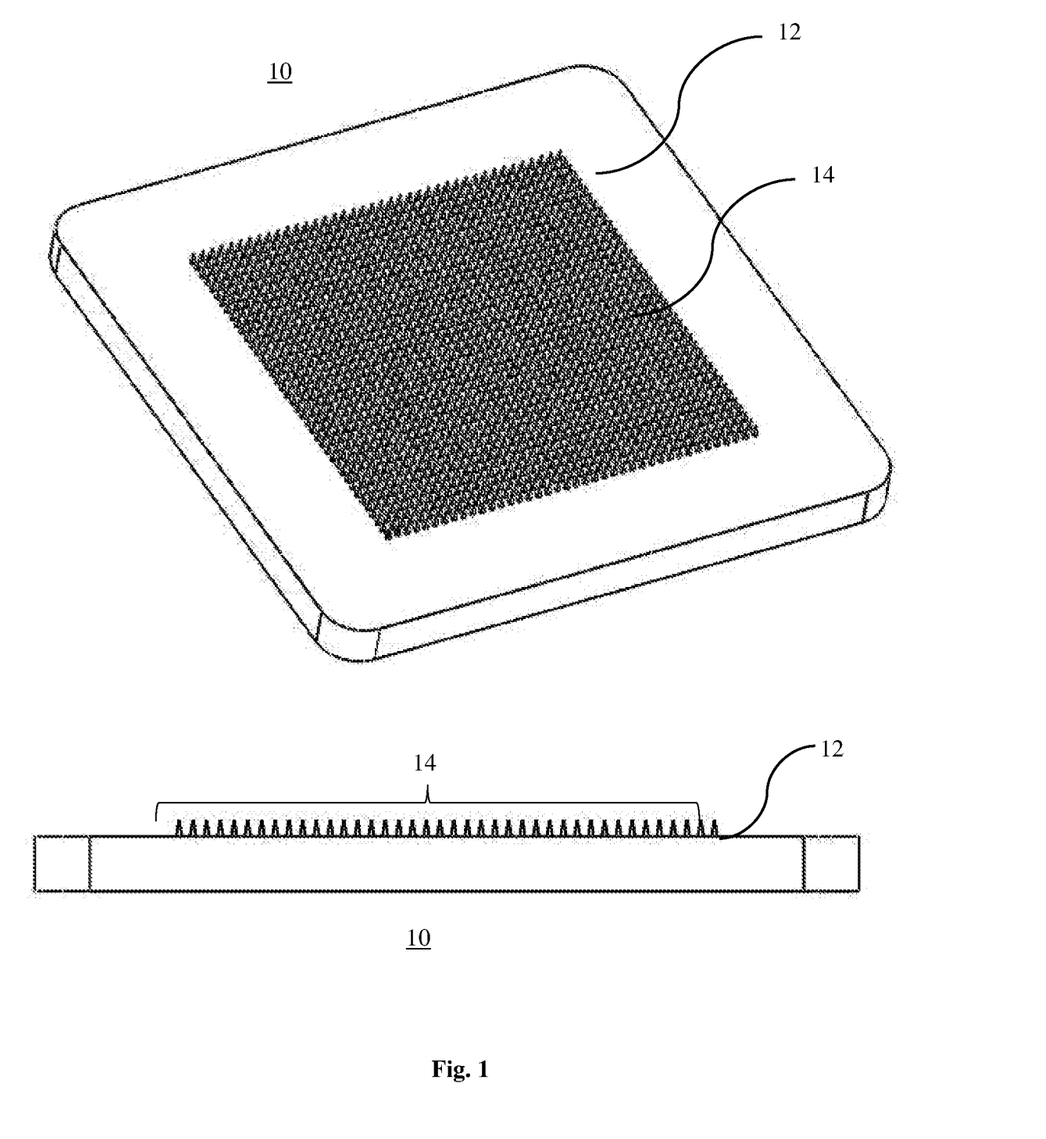
FIG. 1 shows a dissolving microneedle patch 10 comprising a substrate 12 from which a plurality of microneedles 14 extends.

In an embodiment of the present invention, a patch of dissolving microneedles loaded with active ingredients to be applied to skin for treating skin conditions is provided. As seen in FIG. 1, the dissolving microneedle patch 10 comprises a substrate 12 and a plurality of microneedles 14 which extends from the substrate. The dissolving microneedle patch 10 is made of a matrix material and at least one active ingredient such as a corticosteroid, namely triamcinolone (TAC). The matrix material is made of biocompatible materials such as hyaluronic acid (HA), polyvinylpyrrolidone (PVP), or mixture of them, which dissolve rapidly when they are in contact with the inner skin. The active ingredient is loaded onto individual patches with the desirable dosage ranging from 0.01 mg-1.0 mg.

The dissolving microneedle patch 10 may be accompanied by a skin protection coating 20 which has a hole tailored to the target keloid's shape so that the active ingredient can be effectively delivered into the keloid while the excess will be masked out by the skin protection coating 20. The skin protection coating 20 is made of inert material including but not limited to woven or non-woven fabrics, wax, polymer films, etc. and is adhered on the targeted skin site to only expose the keloid to the dissolving microneedle patch 10.

For delivering the active ingredients loaded in the microneedles, the dissolving microneedle patch 10 is applied on the affected skin site (such as a keloid) and is held on with mild pressure for a length of time, e.g. from 10 seconds to 10 minutes.

The application of the dissolving microneedle patch can be carried in several modes, including using a spring applicator and a handle.

Another embodiment of the present invention includes the dissolving microneedle patch 30 being affixed on a skin adhesive 32. The skin protection coating 40 is an external separate piece that is applied on the skin beforehand to expose only the keloid to the dissolving microneedle patch 30. This adhesive dissolving microneedle patch 30 is applied on the skin with fingers and it is adhered on the skin for a length of time. The patient may use his fingers to exert mild pressure on the patch from time to time.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

It is the objective of the present invention to provide a drug delivery solution for the current intradermal injection practice for treating chronic skin conditions such as keloid scars. Currently, patients with keloid scars have to visit dermatologist regularly for the intradermal injections of corticosteroid such as triamcinolone (TAC). As mentioned earlier, a dissolving microneedle patch laded with TAC provides a home-based alternative for the patients because this patch is painless and easy to use. The present invention aims to cater to the uniform delivery of active ingredients across a targeted skin site, including but not limited to a keloid, by plurality of dissolving microneedles. FIG. 1 shows an example of such a drug-laden dissolving microneedle patch 10. As shown in the figure, the patch comprises a substrate 12 from which a plurality of dissolving microneedles 14 extend. The microneedles are typically 100 um to 1,000 um tall, with the peak-to-peak distance of 500 um to 3,000 um. For example, a 10×10 array of microneedle patch with a 500 um peak-to-peak distance will have roughly a 5 mm×5 mm=25 $mm^2$ in area. Due to manufacturing convenience, the dissolving microneedle patch 10 normally has rectangular shapes in sizes, typically ranging from 5 mm×5 mm to 100 mm×100 mm. The active ingredient is loaded onto individual patches with the desirable dosage ranging from 0.001 mg-1.0 mg per $mm^2$, or more particularly 0.001 mg-0.01 mg per $mm^2$.

Figure 2:
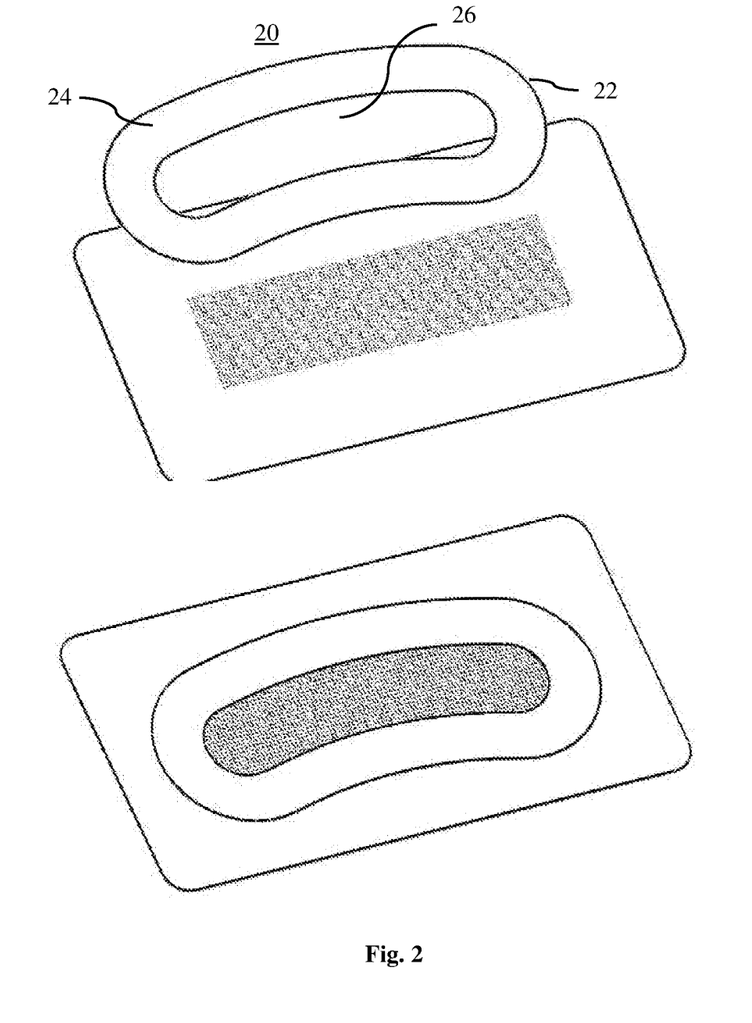
FIG. 2 shows an external skin protection coating 20 having a through hole for only exposing a targeted skin site such as a keloid. The coating 20 comprises a bottom surface 22 having an adhesive coating for affixing onto the skin, a top surface 24 for receiving the microneedles, and a hole 26 to expose a keloid while masking out the normal skin.

Quite often the targeted skin sites have irregular shapes. By applying the rectangular shaped dissolving microneedle patches, the surrounding normally skin will also be injected with the active ingredients, which is not desirable because the normal tissues will be damaged. In order to prevent this undesirable event from happening, the present invention provides a skin protection coating which basically covers the surrounding normal skin with inert material and prevents the dissolving microneedles from penetrating it. FIG. 2 shows an external skin protection coating 20, which comprises a bottom surface 22 coated with skin adhesive, a top surface 24 for receiving the microneedles, and a hole 26 made to expose a keloid. The external skin protection coating 20 is a thin layer of inert material such as woven or non-woven fabric, wax, polymer films, etc. that adheres to the skin before the dissolving microneedles are applied to the skin. The external skin protection coating 20 can take the form of a film that can be worn on a keloid, or it can take the form of a liquid like wax, which takes a liquid form when it is applied on the skin with a brush but rapidly solidifies into a solid layer which firmly adhere to the skin to mask out the normal skin and protect it from delivery of TAC by the microneedles.

Figure 3:
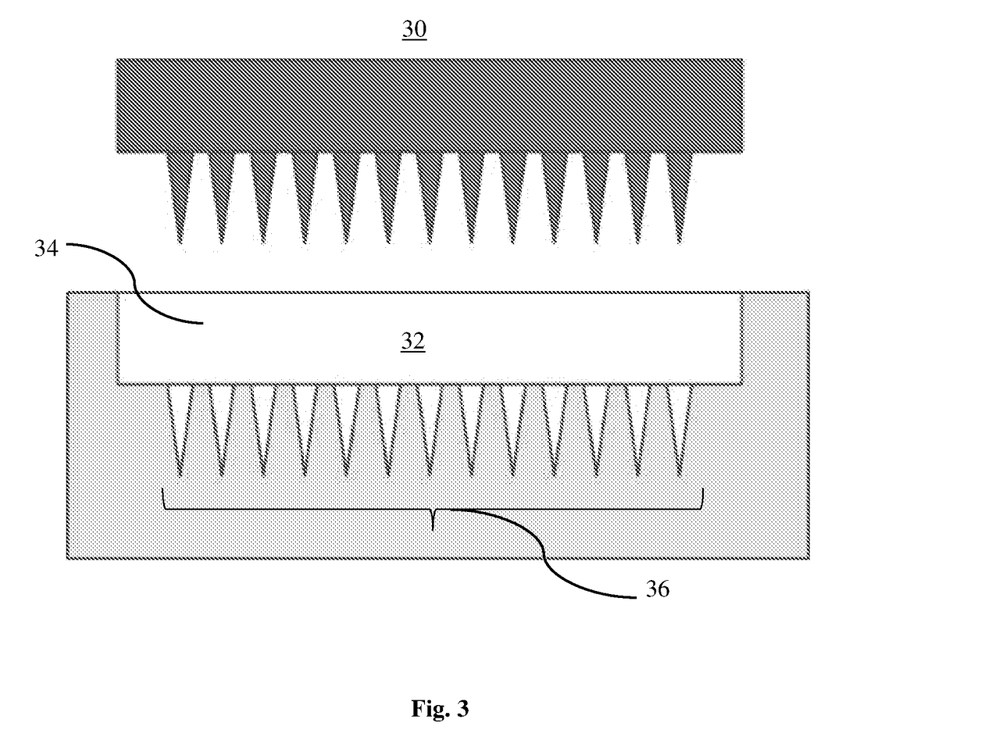
FIG. 3 shows a dissolving microneedle patch 30 and a microneedle template 32 having a cavity 34 and a plurality of microneedle cavities 36.

The fabrication of the dissolving microneedle patch is reported in patent document WO 2015/122838A1, which is incorporated by reference in its entirety herein. FIG. 3 shows the process flow of making a dissolving microneedle patch 30 on a microneedle template 32. The microneedle template 32 comprises a cavity 34 and a plurality of microneedle cavities 36. The dissolving microneedle patch 30 is made of a matrix material and at least one active ingredient such as a corticosteroid, namely triamcinolone (TAC). The matrix material is made of bio-compatible materials such as hyaluronic acid (HA), polyvinylpyrrolidone (PVP), or mixture of them, which dissolve rapidly when they are in contact with the inner skin. The active ingredient triamcinolone acetonide TAC is only mildly soluble in water.

Fabrication of Dissolving Microneedle Patch. In one example, the active ingredient TAC is pre-mixed with the matrix material and the mixture is cast onto the microneedle template 32 (FIG. 3) to form the dissolving microneedle patch. The microneedle template has a cavity 34 with dimensions of 8 mm×8 mm×1 mm (height), or 64 ul in volume, which further comprises a plurality of microneedle cavities 36. The matrix material is HA 0.6 g/ml and the active ingredient is TAC 10 mg/ml. The mixing ratio is HA:TAC=5:1. 64 ul of the mixture is loaded into the cavity 34 and the microneedle template 32 is subjected to a centrifugal force at 3,000-5,000 RPM for 1-2 minutes. The centrifugal force will push the mixture comprising TAC into the microneedle cavities 36. Since TAC is not soluble in water, a considerable amount of TAC in the cavity 34 is forced to fill the microneedle cavities 36.

Alternatively, the active ingredient and the matrix material can be loaded individually into the cavity 34 of the microneedle template 32. The matrix material may be 50 ul of HA at 0.6 g/ml and the active ingredient may be 10 ul of TAC at 10 mg/ml, which makes up 0.1 mg per patch. The loaded microneedle template 32 is then subjected to a centrifugal force of 3,000 RPM to 5,000 RPM for 1-2 minutes to fill up the microneedle cavities 36. Due to the fact that TAC is insoluble, the centrifuging step distributes TAC across the microneedle cavities 36 evenly and pushes TAC into the microneedle cavities 36. Subsequently, the filled microneedle template will be left in a controlled environment so that the microneedle patch solidifies. The solidification duration in room temperature typical ranges from 4-16 hours. Finally, the solidified dissolving microneedle patch 30 is de-molded from the microneedle template 32.

Figure 4:
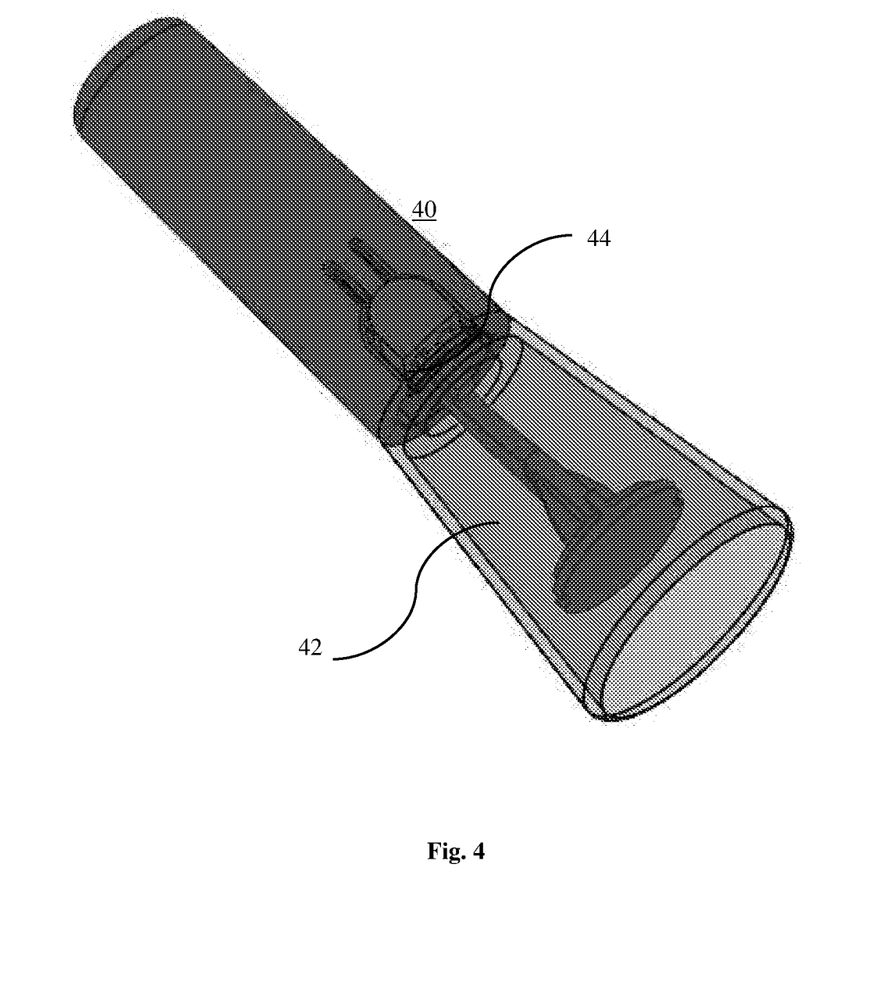
FIG. 4 shows a spring applicator 40 which can be used to apply the dissolving microneedle patch on the skin, comprising a transparent compressor cap 42 and a trigger button 44.

Application of Dissolving Microneedle Patches on the Skin. The application of dissolving microneedle patches on the skin can be achieved by several methods. FIG. 4 shows a spring applicator 40 which is used for applying a dissolving microneedle patch on the skin. The spring applicator 40 comprises a transparent compressor cap 42 for fixing and tensioning the skin site prior to application and a trigger button 44 is pushed to release the spring for applying the dissolving microneedle patch 46 onto the skin at high speed. The penetration speed of the spring applicator 40 is roughly 2 m/s and the impact force is 1.0-1.6N. The use of spring applicator warrants consistency and repeatability of the application of dissolving microneedle patches.

Figure 5:
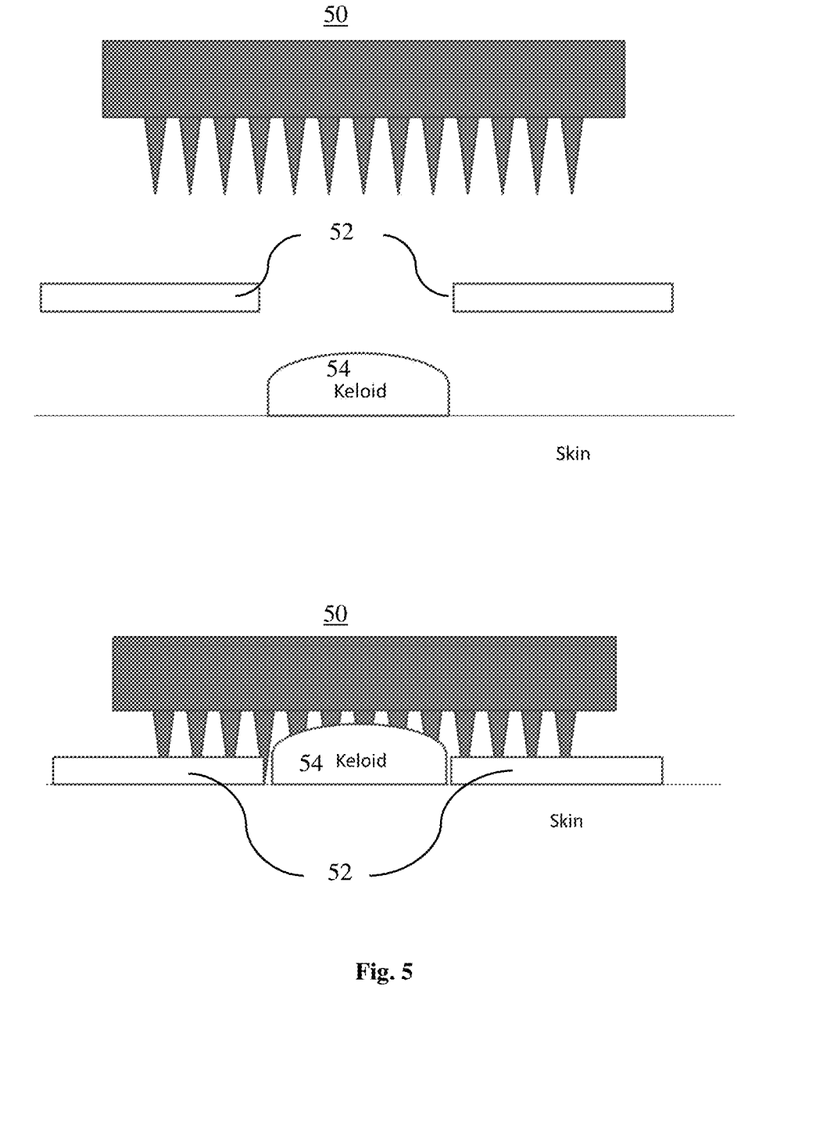
FIG. 5 shows schematically the application of a dissolving microneedle patch 50 onto a skin site such as a keloid 52 which is masked out by a skin protection coating 54.

In the case where the targeted skin site is a large area, the spring applicator is not able to apply large patches. Therefore, large patches can only be applied by hands. However, as mentioned earlier, large patches may overreach the normal skin area and deliver corticosteroid to the normal skin site, which is undesirable. FIG. 5 shows a schematic process flow of how a dissolving microneedle patch 50 and an external skin protection coating 52 are applied to target only the affected skin sites such as keloids 54. The external skin protection coating 52 masks out the normal skin and only exposes the keloid to receive the microneedles. The external skin protection coating 52 can take the form of a skin adhesive, which has one surface having skin adhesive for affixation on the skin and another open surface for receiving microneedles. Alternatively, the external skin protection coating 52 can take the form of a wax, which can be in liquid form and is applied onto the skin with a brush, and rapidly solidifies to form a rigid layer on the skin to receive microneedles.

Clinical Trial. The dissolving microneedle patches were made and loaded with 0.1 mg of TAC and were applied with the spring applicator. The trial was carried out at National Skin Centre in Singapore. This was a single-blinded, intra-individual randomized controlled clinical trial where two keloids on each subject were randomized to the following treatment groups:

1. Control group: No treatment
2. Dissolving microneedles group: Triamcinolone-embedded, dissolving hyaluronic acid microneedles At baseline, volume measurements and patient assessments of pain and itch were recorded. Subjects were treated with the dissolvable microneedles over 4 weeks and measurements were repeated. A final visit was scheduled at 4 weeks post-treatment and measurements taken again (Table 1).

TABLE 1

| Study Schedule | |
|---|---|
| Visits | Action taken |
| Baseline (Week 0) | Patient assessment and randomization Measurements |
| 1$^{st}$ Visit (Week 4) | Review - conclusion of treatment Measurements |
| 2$^{nd}$ Visit (Week 8) | Review and measurements |

A total of 17 patients, comprising of 15 (88.2%) males and 2 (11.8%) females were enrolled into the study. A majority of the patients were Chinese (n=12, 70.6%), Malay (n=4, 23.5%), and others (n=1, 5.9%). All 17 patients completed the study.

Figure 6:
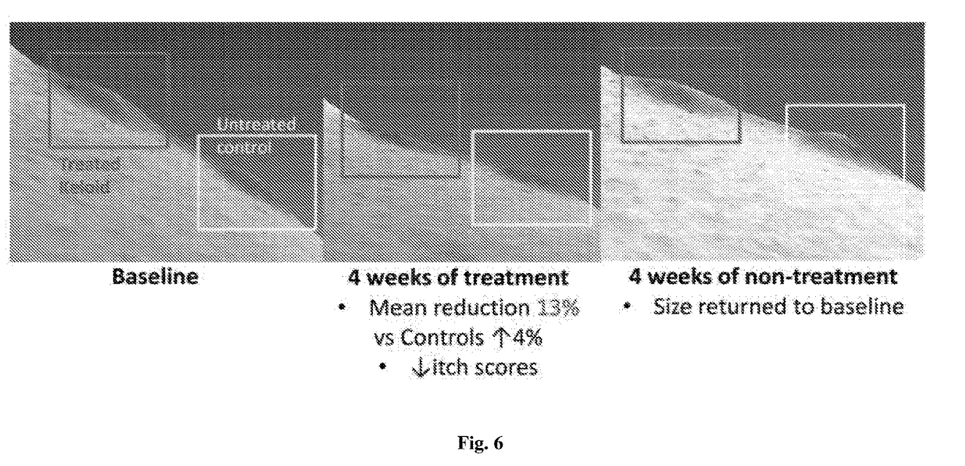
FIG. 6 shows a keloid treated with the dissolving microneedles versus a control keloid on the same patient—at baseline, 4 weeks after treatment, and after another 4 weeks of withheld treatment.

After applying the treatment for 4 weeks, significant reduction in mean keloid size was seen in the Dissolving microneedles group from 171.6 mm3 in Visit 1 to 149.6 mm$^3$ in Visit 2 (p-value 0.001, Table 2, FIG. 6). The reduction in the Dissolving microneedles group (mean change: −22.1±28.0) was greater than the Control group (mean change: 6.7±58.3, p-value=0.034). In the subsequent 4 weeks, when no treatment was given from Visit 2 to Visit 3, it was observed that the keloids treated in the Dissolving microneedles group (p-value=0.005) grew back in size.

TABLE 2

| | Keloid size/volume by Visit and Intervention | | | | | |
|---|---|---|---|---|---|---|
| | Visit 1 (n = 17) | Visit 2 (n = 17) | Visit 3 (n = 17) | Change from Visit 1 to 2 (n = 17) | Change from Visit 2 to 3 (n = 17) | Change from Visit 1 to 3 (n = 17) |
| | | | Keloid Size (mm$^3$) | | | |
| Control group | | | | | | |
| Mean ± SD | 182.0 ± 330.1 | 188.6 ± 376.1 | 186.8 ± 368.4 | 6.7 ± 58.3 | −1.9 ± 11.7 | 4.8 ± 55.1 |
| Median (min, max) | 66.3 (7.0, 1341.2) | 58.2 (5.4, 1563.2) | 57.0 (7.5, 1537.5) | −1.0 (−67.7, 222.0) | 1.3 (−27.9, 14.1) | 0.5 (−95.5, 196.3) |
| p-value for comparing each visit and subsequent visit for intervention = Control | — | — | — | 0.545 | 0.498 | 0.663 |
| Dissolving microneedle group | | | | | | |
| Mean ± SD | 171.6 ± 432.6 | 149.6 ± 418.2 | 172.3 ± 448.8 | −22.1 ± 28.0 | 22.8 ± 38.5 | 0.7 ± 25.1 |
| Median (min, max) | 35.7 (8.4, 1826.9) | 28.2 (3.0, 1761.2) | 38.8 (7.2, 1892.3) | −7.2 (−75.7, 19.8) | 5.9 (−1.9, 131.2) | 0.6 (−50.2, 65.4) |
| p-value for comparing each visit and subsequent visit | — | — | — | 0.001 | 0.005 | 0.917 |

TABLE 2-continued

Keloid size/volume by Visit and Intervention

|  | Visit 1 (n = 17) | Visit 2 (n = 17) | Visit 3 (n = 17) | Change from Visit 1 to 2 (n = 17) | Change from Visit 2 to 3 (n = 17) | Change from Visit 1 to 3 (n = 17) |
|---|---|---|---|---|---|---|
|  |  |  | Keloid Size (mm³) |  |  |  |
| for intervention = Dissolving |  |  |  |  |  |  |
| p-value for comparing each visit and subsequent visit between Dissolving and Control | — | — | — | 0.034 | 0.001 | 0.765 |

Note:
Keloid Size (mm³) was based on the mean of 3 measurements.

Subjects from the Dissolving microneedles group experienced significantly lesser itch after 4 weeks of treatment (Table 3) from 1.7±2.3 at Visit 1 to 1.0±1.9 at Visit 2 (p-value=0.005) and the itch reduction (mean change: −0.7±1.1) was more significant than the Control group (mean change: 0.4±2.0, p-value=0.005).

TABLE 3

Itch score on a 1-10 numerical scale by Visit and Intervention

|  | Visit 1 (n = 17) | Visit 2 (n = 17) | Visit 3 (n = 17) | Change from Visit 1 to 2 (n = 17) | Change from Visit 2 to 3 (n = 17) | Change from Visit 1 to 3 (n = 17) |
|---|---|---|---|---|---|---|
|  |  |  | Itch score |  |  |  |
| Control group |  |  |  |  |  |  |
| Mean ± SD | 1.8 ± 2.3 | 2.2 ± 2.7 | 1.4 ± 2.2 | 0.4 ± 2.0 | −0.8 ± 1.6 | −0.4 ± 1.8 |
| Median (min, max) | 0.0 (0.0, 7.0) | 1.0 (0.0, 8.0) | 0.0 (0.0, 7.0) | 0.0 (−2.0, 8.0) | 0.0 (−4.0, 2.0) | 0.0 (−3.5, 4.0) |
| p-value for comparing each visit and subsequent visit for intervention = Control | — | — | — | 0.329 | 0.036 | 0.402 |
| Dissolving microneedle group |  |  |  |  |  |  |
| Mean ± SD | 1.7 ± 2.3 | 1.0 ± 1.9 | 0.9 ± 1.9 | −0.7 ± 1.1 | −0.1 ± 0.6 | −0.8 ± 1.3 |
| Median (min, max) | 0.0 (0.0, 7.5) | 0.0 (0.0, 7.5) | 0.0 (0.0, 7.5) | 0.0 (−3.5, 1.0) | 0.0 (−1.0, 1.5) | 0.0 (−3.5, 1.5) |
| p-value for comparing each visit and subsequent visit for intervention = Dissolving | — | — | — | 0.005 | 0.507 | 0.002 |
| p-value for comparing each visit and subsequent visit between Dissolving and Control | — | — | — | 0.005 | 0.046 | 0.272 |

What is claimed is:

1. A dissolving microneedle patch, comprising:
   a matrix material and an active pharmaceutical ingredient, wherein the active pharmaceutical ingredient is a corticosteroid; and
   an external skin protection coating having a through hole configured for only exposing a targeted skin site, said external skin protection coating is configured for protecting normal skin outside the targeted skin site from receiving the microneedles;
   wherein the external skin protection coating comprises a solidified form of a liquid wax applied on skin that forms a protective layer.

2. The dissolving microneedle patch of claim 1, wherein the matrix material comprises hyaluronic acid.

3. The dissolving microneedle patch of claim 1, wherein the matrix material comprises polyvinylpyrrolidone.

4. The dissolving microneedle patch of claim 1, wherein the corticosteroid is triamcinolone acetonide.

5. The dissolving microneedle patch of claim 1, wherein the corticosteroid dose ranges from 0.01 mg to 1.0 mg per patch.

6. The dissolving microneedle patch of claim 1, wherein the external skin protection coating further comprises a first surface to be adhered to skin and a second surface for receiving the microneedles.

7. The dissolving microneedle patch of claim 1, wherein the external skin protection coating is made of a skin adhesive having a first surface coated with skin adhesive and a second surface to receive the microneedles.

* * * * *